(12) United States Patent
Igersheim et al.

(10) Patent No.: US 8,846,980 B2
(45) Date of Patent: Sep. 30, 2014

(54) PROCESS FOR THE PRODUCTION OF AN ALKYL HYDROPEROXIDE

(75) Inventors: Françoise Igersheim, Lyons (FR); Stéphane Streiff, Lyons (FR); Serge Veracini, Lyons (FR)

(73) Assignee: Rhodia Operations, Aubervilliers (FR)

( * ) Notice: Subject to any disclaimer, the term of this patent is extended or adjusted under 35 U.S.C. 154(b) by 11 days.

(21) Appl. No.: 13/574,640

(22) PCT Filed: Jan. 14, 2011

(86) PCT No.: PCT/EP2011/050470
§ 371 (c)(1),
(2), (4) Date: Oct. 11, 2012

(87) PCT Pub. No.: WO2011/089075
PCT Pub. Date: Jul. 28, 2011

(65) Prior Publication Data
US 2013/0046115 A1    Feb. 21, 2013

(30) Foreign Application Priority Data

Jan. 21, 2010  (FR) ...................................... 10 50385

(51) Int. Cl.
*C07C 407/00* (2006.01)
(52) U.S. Cl.
CPC ........... *C07C 407/00* (2013.01); *C07C 2101/14* (2013.01)
USPC ........................................................ 568/570
(58) Field of Classification Search
USPC ........................................................ 568/570
See application file for complete search history.

(56) References Cited

U.S. PATENT DOCUMENTS

| 3,479,394 A | 11/1969 | Brunie et al. |
| 3,551,482 A | 12/1970 | Gey et al. |
| 3,719,706 A | 3/1973 | Brunie et al. |
| 3,956,397 A * | 5/1976 | Billet et al. ................... 568/576 |
| 4,055,600 A | 10/1977 | Langley et al. |
| 4,877,903 A | 10/1989 | Costantini et al. |
| 2007/0073088 A1 | 3/2007 | Simon et al. |
| 2013/0046115 A1 | 2/2013 | Igersheim et al. |

FOREIGN PATENT DOCUMENTS

| EP | 0404417 A1 | 12/1990 |
| FR | 1527390 | 6/1967 |
| FR | 2291956 A1 | 6/1976 |
| GB | 777087 | 6/1957 |
| GB | 816200 | 7/1959 |
| GB | 964869 | 7/1964 |
| GB | 1112837 | 5/1968 |
| GB | 1191573 | 5/1970 |
| JP | 48-31091 B1 | 9/1973 |
| JP | 2001-515098 A | 9/2001 |
| JP | 2007-502318 A | 2/2007 |
| JP | 2008-143942 A | 6/2008 |
| WO | 99/11740 A1 | 3/1991 |

OTHER PUBLICATIONS

International Search Report issued on Apr. 21, 2011 and an English language translation of the Search Report.

* cited by examiner

*Primary Examiner* — Sikarl Witherspoon
(74) *Attorney, Agent, or Firm* — Dentons US LLP

(57) ABSTRACT

A method for preparing an alkyl hydroperoxide obtained by the oxidation of a saturated hydrocarbon using oxygen, preferably of a saturated cyclic hydrocarbon, is described. Also described, is a method for preparing cyclohexyl hydroperoxide by oxidizing cyclohexane with molecular oxygen or a gas containing molecular oxygen preferably in the absence of a catalyst.

3 Claims, No Drawings

PROCESS FOR THE PRODUCTION OF AN ALKYL HYDROPEROXIDE

CROSS-REFERENCE TO PRIOR APPLICATIONS

This application is a National Stage of PCT/EP2011/050470, filed Jan. 14, 2011, and designating the United States (published in French on Jul. 28, 2011, as WO 2011/089075 A1; the title and abstract were published in English), which claims priority of FR 1050385, filed Jan. 21, 2010, each hereby expressly incorporated by reference in its entirety and each assigned to the assignee hereof.

The present invention relates to a process for preparing an alkyl hydroperoxide obtained by oxidation, with oxygen, of a saturated hydrocarbon, preferably of a saturated cyclic hydrocarbon.

It relates more particularly to the production of cyclohexyl hydroperoxide obtained by oxidation of cyclohexane with molecular oxygen or a gas containing molecular oxygen, preferably in the absence of catalyst.

The production of cyclohexyl hydroperoxide is generally the first step in the process for producing cyclohexanone and/or cyclohexanol.

These cyclohexanone and cyclohexanol compounds, alone or as mixtures, are important starting materials for the production of adipic acid and of epsilon-caprolactam, which are monomers for the production of polyamide thermoplastics, or in the synthesis of polyurethane materials, polyester materials or analogues.

Specifically, the main process for producing adipic acid which is used on the industrial scale consists in oxidizing cyclohexane, using molecular oxygen, to give an alcohol and/or ketone. The mixture of ketone and alcohol is then oxidized to give adipic acid using nitric acid.

In one of the embodiments of the process for oxidizing cyclohexane to give an alcohol/ketone, the cyclohexane is oxidized in a first step, in the presence or absence of catalyst, to give mainly cyclohexyl hydroperoxide, this hydroperoxide being converted to an alcohol/ketone in a second step. This first step for oxidizing cyclohexane is generally carried out in a two-phase gas/liquid medium, the oxidizing gas, namely oxygen or a gas containing oxygen, being introduced into the liquid medium in reactors consisting of one or more partitioned or nonpartitioned bubble columns, mounted in series when there is more than one of them, operating either in co-current mode or in counter-current mode with respect to the direction of movement of the liquid phase constituted mainly of cyclohexane in the liquid state. This step is in particular described in patents GB 777087, 1112837, 964869 and 1191573, U.S. Pat. Nos. 3,479,394 and 4,877,903.

The reaction medium recovered on exiting the oxidation step contains cyclohexane which has not reacted and the products formed during the oxidation.

These oxidized products can be classified into two categories:
- a first category consisting of the compounds which are or can be converted to a cyclic alcohol/ketone downstream in the process. In the case of cyclohexane oxidation, these "olonogenic" products are cyclohexanol, cyclohexanone and cyclohexyl hydroperoxide, and
- a second category which comprises the oxidized products which cannot be converted to a cyclic alcohol or ketone, said products resulting from opening of the hydrocarbon-based ring during the oxidation process, such as monocarboxylic or dicarboxylic acids. For example, still in the case of cyclohexane oxidation, these "non-olonogenic" oxidized products are adipic acid, hydroxy acids such as 6-hydroxyhexanoic acid, hydroperoxy acids such as 6-hydroperoxyhexanoic acid, or cyclic products bearing two oxygenated functions, such as hydroxycyclohexanols or hydroxycyclohexanones.

The products of the first category are not very water-soluble. Conversely, the products of the second category are water-soluble and can be extracted by washing with water.

In the processes used, a part of the cyclohexane which has not reacted in the oxidation step is separated from the reaction medium and recycled to the oxidation reactors.

The resulting reaction medium is then subjected to washing or extraction with water in order to separate the water-soluble products generally belonging to the second category of oxidized products.

The reaction medium thus recovered contains mainly cyclohexyl hydroperoxide in solution in cyclohexane, with other oxidized products, belonging mainly to the first category described above.

This solution of cyclohexyl hydroperoxide is advantageously introduced into a decomposition or deperoxidation step in the presence of catalyst, in order to convert the hydroperoxide to ketone and alcohol.

The process of extracting with water the oxidized products belonging to the second category has certain drawbacks; in particular, the extraction is not completely selective. Thus, "olonogenic" oxidized products, said products belonging to the first category, are partially extracted by the aqueous phase, thereby reducing the yield and the cost-effectiveness of the process.

One of the aims of the present invention is to remedy these drawbacks by proposing a solution which makes it possible in particular to greatly reduce the amount of oxidized products of the first category in the aqueous phase and therefore to improve the cost-effectiveness of the process.

To this effect, the invention proposes a process for the manufacture of alkyl hydroperoxide by oxidation of a saturated hydrocarbon using molecular oxygen, comprising the following successive steps:
  oxidation of the hydrocarbon using oxygen,
  separation of at least a part of the nonoxidized hydrocarbon from the oxidation reaction medium and recycling of said nonoxidized hydrocarbon to the oxidation step,
  washing, with water, of the oxidation reaction medium recovered after the separation of at least a part of the nonoxidized hydrocarbon, in order to extract the water-soluble oxidized products formed during the oxidation ("non-olonogenic" products when the hydrocarbon is cyclohexane), and to recover an organic phase comprising the nonoxidized hydrocarbon, the alkyl hydroperoxide and water-insoluble oxidized products ("olonogenic" products when the hydrocarbon is cyclohexane).

According to the invention, the washing step is characterized in that it is carried out in a counter-current liquid/liquid extraction column, with the washing water being fed at the top of the column and the reaction medium to be treated/washed being fed at an intermediate position of the column, and in that the saturated hydrocarbon to be oxidized is fed into the washing column at a position located downstream of the position for feeding the medium to be treated/washed, with respect to the direction of movement of the water, i.e. the saturated hydrocarbon to be oxidized is fed into the washing column at a level below that at which the medium to be washed is fed.

According to one preferred characteristic of the invention, the hydrocarbon to be oxidized is selected from the group consisting of cyclohexane, cyclooctane, cyclododecane, decalin or the like. Cyclohexane is the preferred hydrocarbon.

The hydrocarbon fed in the washing operation is preferably a hydrocarbon which does not originate from a recycling loop of the oxidation process, but which is a hydrocarbon referred to as "new" since it does not contain oxidized products and originates from the hydrocarbon supplied for the process.

According to another characteristic of the invention, the oxidation process can be carried out in the absence of catalyst or in the presence of catalyst.

The feeding of hydrocarbon such as cyclohexane into the downstream (lower) part of the column for extraction or washing with water, with respect to the direction of movement of the water, makes it possible to extract, from the aqueous phase, in this downstream part of the column, the oxidized products which are water-insoluble or which have low water solubility. These products are in particular the "olonogenic" oxidized compounds such as cyclohexanol, cyclohexanone and cyclohexyl hydroperoxide.

Thus, the feeding of hydrocarbon such as cyclohexane makes it possible in particular to very substantially reduce the concentrations of cyclohexanol, cyclohexanone and cyclohexyl hydroperoxide in the effluent aqueous phase.

By way of indication, this concentration of cyclohexyl hydroperoxide, cyclohexanol or cyclohexanone in the aqueous phase exiting the extraction column is of the order of several per cent by weight for each of the compounds without feeding of hydrocarbon into the washing column. The process of the invention makes it possible to reduce this concentration to a few hundred ppm.

Another advantage of the invention is that of treating, by aqueous washing, at least a part of the new hydrocarbon to be oxidized before it is fed into the oxidation step. This is because hydrocarbons transported and stored in metallic containers can contain metallic impurities such as oxides or the like. These metallic compounds impair the cyclohexane oxidation process, in particular when it is implemented without catalyst in order to produce cyclohexyl hydroperoxide. This is because the decomposition of cyclohexyl hydroperoxide is catalysed by metals and metallic compounds.

Consequently, the process for producing cyclohexyl hydroperoxide advantageously comprises a step of aqueous washing of the new cyclohexane in order to eliminate these metallic compounds before feeding of the cyclohexane in the oxidation step.

In the process of the invention, the new hydrocarbon, such as cyclohexane, fed into the extraction column, on the one hand, makes it possible to extract, from the aqueous phase, the "olonogenic" oxidized compounds with low water solubility and, on the other hand, undergoes washing with water, with extraction of the metallic compounds that may be contained in the hydrocarbon.

The new hydrocarbon thus washed is introduced into the oxidation step, preferably with the hydrocarbon recycled via the various recycling steps of the process.

The process of the invention therefore makes it possible to reduce the losses of exploitable oxidized products by decreasing the concentration present in the aqueous phase exiting the washing step, and also to decrease the aqueous washing capacity to be provided for in order to wash the hydrocarbon before feeding into the oxidation step.

The washing step of the process of the invention can be carried out in any suitable device and is preferably carried out continuously.

When the hydrocarbon under consideration is cyclohexane, the washing is carried out at a temperature of from 80 to 100° C.

Other details and advantages of the invention become clearly apparent in view of the examples given below, only by way of illustration.

EXAMPLE 1

In a washing column comprising forty actual plates and operating at a pressure of 2 bar, a reaction mixture originating from the oxidation of cyclohexane using oxygen, carried out in the absence of catalyst, is fed at the middle of the column. The washing water is fed at the top of the column with a flow rate corresponding to 5.5% by weight of the stream of reaction mixture introduced into the column. The new cyclohexane (not originating from a recycling) is fed at the bottom of the column with a flow rate corresponding to 75% by weight of the flow rate of washing water introduced at the top of the column. The aqueous effluent containing 22% by weight of organic compounds is recovered at the base of the column. The concentration of "olonogenic" products in the aqueous effluent is less than 500 ppm (concentration of cyclohexanol/cyclohexanone about 40 ppm, concentration of cyclohexyl hydroperoxide about 350 ppm).

The washing of the reaction medium is, according to the process of the invention, carried out with a very small loss of "olonogenic" products.

EXAMPLE 2

In a washing column comprising eighty actual plates and operating at a pressure of 2 bar, a reaction mixture originating from the oxidation of cyclohexane using oxygen, carried out in the absence of catalyst, is fed at the middle of the column. The washing water is fed at the top of the column with a flow rate corresponding to 5.1% by weight of that of the reaction mixture to be washed, still fed at the middle of the column. The new cyclohexane (not originating from a recycling) is fed at the bottom of the column with a flow rate corresponding to 70% by weight of the flow rate of washing water introduced at the top of the column. The aqueous effluent containing 23% by weight of organic compounds is recovered at the base of the column. The concentration of "olonogenic" products in the aqueous effluent is less than 1400 ppm (concentration of cyclohexanol/-cyclohexanone less than 50 ppm, concentration of cyclohexyl hydroperoxide about 1350 ppm). The washing of the reaction medium is, according to the process of the invention, carried out with a very small loss of "olonogenic" products.

EXAMPLE 3

In a washing column comprising eighty actual plates and operating at a pressure of 2 bar, a reaction medium originating from the oxidation of cyclohexane using oxygen, carried out in the absence of catalyst, is fed at the middle of the column. The washing water is fed at the top of the column with a flow rate corresponding to 4.3% by weight of that of the reaction mixture to be washed, still fed at the middle of the column. The new cyclohexane (not originating from a recycling) is fed at the bottom of the column with a flow rate corresponding to 83% by weight of the flow rate of washing water introduced at the top of the column. The aqueous effluent containing 19% by weight of organic compounds is recovered at the base of the column. The concentration of "olonogenic" products in the aqueous effluent is less than 1600 ppm (concentration of cyclohexanol/-cyclohexanone less than 50 ppm, concentration of cyclohexyl hydroperoxide about 1500 ppm). The washing of the reaction medium is, according to the process of the invention, carried out with a very small loss of "olonogenic" products.

EXAMPLE 4

In a washing column comprising eighty actual plates and operating at a pressure of 2 bar, a reaction medium originating from the oxidation of cyclohexane using oxygen, carried out in the absence of catalyst, is fed at the middle of the column. The washing water is fed at the top of the column with a flow rate corresponding to 4.7% by weight of that of the reaction mixture to be washed, still fed at the middle of the column. The new cyclohexane (not originating from a recycling) is fed at the bottom of the column with a flow rate corresponding to 82% by weight of the flow rate of washing water introduced at the top of the column. The aqueous effluent containing 20% by weight of organic compounds is recovered at the base of the column. The concentration of "olonogenic" products in the aqueous effluent is less than 1600 ppm (concentration of cyclohexanol/-cyclohexanone less than 50 ppm, concentration of cyclohexyl hydroperoxide about 1470 ppm). The washing of the reaction medium is, according to the process of the invention, carried out with a very small loss of "olonogenic" products.

The invention claimed is:

1. A process for the production of alkyl hydroperoxide by oxidation of a saturated hydrocarbon using molecular oxygen, the process comprising:
   oxidizing the hydrocarbon using oxygen,
   separating at least a part of a nonoxidized hydrocarbon from the reaction medium and recycling of the nonoxidized hydrocarbon to the oxidation step, and
   washing, with water, an oxidation reaction medium recovered after the separation of at least a part of the nonoxidized saturated hydrocarbon, in order to extract water-soluble oxidized byproducts and to recover an organic phase comprising the alkyl hydroperoxide, the nonoxidized hydrocarbon and water-insoluble oxidized products,
   wherein:
   the washing step is carried out in a counter-current liquid/liquid extraction column, with the washing water being fed at the top of the column and the reaction medium to be washed, comprising the alkyl hydroperoxide, being fed at an intermediate position of the column;
   the saturated hydrocarbon to be oxidized is fed into the washing column at a level below that at which the medium to be washed is fed;
   the hydrocarbon is selected from the group consisting of cyclohexane, cyclooctane, cyclododecane and decalin;
   the hydrocarbon fed in the washing operation is a hydrocarbon which does not originate from a recycling loop of the oxidation process; and
   the hydrocarbon thus washed is introduced into the oxidation step.

2. The process as defined by claim 1, wherein the alkyl hydroperoxide is cyclohexyl hydroperoxide, and the saturated hydrocarbon is cyclohexane.

3. The process as defined by claim 2, wherein the washing is carried out at a temperature of from 80° C. to 100° C.

* * * * *